(12) United States Patent
Kawano et al.

(10) Patent No.: US 9,566,428 B2
(45) Date of Patent: Feb. 14, 2017

(54) ARTIFICIAL SENSORY EPITHELIUM (71) Applicant: OSAKA UNIVERSITY, Osaka (JP)

(72) Inventors: Satoyuki Kawano, Osaka (JP); Juichi Ito, Kyoto (JP); Takayuki Nakagawa, Kyoto (JP); Hirofumi Shintaku, Kyoto (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 14/422,873

(22) PCT Filed: Aug. 30, 2013

(86) PCT No.: PCT/JP2013/073305
§ 371 (c)(1),
(2) Date: Feb. 20, 2015

(87) PCT Pub. No.: WO2014/034843
PCT Pub. Date: Mar. 6, 2014

(65) Prior Publication Data
US 2015/0238753 A1    Aug. 27, 2015

(30) Foreign Application Priority Data

Aug. 31, 2012  (JP) .................. 2012-191109

(51) Int. Cl.
*A61N 1/05*  (2006.01)
(52) U.S. Cl.
CPC .................. *A61N 1/0541* (2013.01)
(58) Field of Classification Search
None
See application file for complete search history.

(56) References Cited

U.S. PATENT DOCUMENTS

| 5,061,282 A | 10/1991 | Jacobs |
| 5,999,859 A | 12/1999 | Jolly |
| 2003/0012390 A1 | 1/2003 | Franks |

(Continued)

FOREIGN PATENT DOCUMENTS

| JP | 2001-514553 A | 9/2001 |
| JP | 2009-525792 A | 7/2009 |
| WO | 2011/150429 A2 | 12/2011 |

OTHER PUBLICATIONS

International Search Report; PCT/JP2013/073305; Sep. 24, 2013.
(Continued)

*Primary Examiner* — Brian T Gedeon
*Assistant Examiner* — Ankit D Tejani
(74) *Attorney, Agent, or Firm* — Studebaker & Brackett PC (57) ABSTRACT

An artificial sensory epithelium (1) to be embedded in a cochlea (301) of a patient includes a piezoelectric film (2) and multitude microelectrodes (3), (3), . . . arranged on the cochlea. The piezoelectric film is arranged along a basilar membrane (306) in the cochlea. A portion of the piezoelectric film that corresponds to a portion of the basilar membrane that is induced to vibrate by sound waves coming from outside the cochlea vibrates. A microelectrode of the microelectrodes that is arranged on the portion of the piezoelectric film provides electric stimuli to spiral ganglion neurons (311). The artificial sensory epithelium preferably includes a support member (4) configured to support the piezoelectric film and be fixable in the cochlea.

14 Claims, 7 Drawing Sheets

(56) References Cited

U.S. PATENT DOCUMENTS

| | | |
|---|---|---|
| 2003/0234595 A1 | 12/2003 | Takahashi et al. |
| 2009/0030486 A1 | 1/2009 | Klefenz |
| 2009/0112288 A1 | 4/2009 | Hur et al. |
| 2010/0179615 A1* | 7/2010 | Zhang ................ A61N 1/36032 607/57 |
| 2011/0295331 A1 | 12/2011 | Wells et al. |

OTHER PUBLICATIONS

Inaoka, T. et al.; "Piezoelectric materials mimic the function of the cochlear sensory epithelium"; Proceedings of the National Academy of Sciences of the United States of America; Nov. 8, 2011; vol. 88, No. 45; pp. 18390-18395.

The extended European search report issued by the European Patent Office on Apr. 21, 2016, which corresponds to European Patent Application No. 13833073.3-1666 and is related to U.S. Appl. No. 14/422,873.

H. Shintaku et al.; "Development of piezoelectric acoustic sensor with frequency selectivity for artificial cochlea"; Sensors and Actuators A: Physical; Mar. 1, 2010; pp. 183-192; vol. 158; No. 2; Elesevier Sequoia; Lausanne, CH.

* cited by examiner

ARTIFICIAL SENSORY EPITHELIUM

TECHNICAL FIELD

The present invention relates to artificial sensory epitheliums to be embedded in a cochlea.

BACKGROUND ART

Hearing loss that is a hearing impairment is divided into conductive hearing loss and sensorineural hearing loss. The conductive hearing loss is caused due to a disorder of an outer ear or a middle ear in sound conduction. The sensorineural hearing loss is caused mostly due to a disorder of an inner ear. While improvements through surgery can be expected in the conductive hearing loss, an auxiliary auditory device such as a hearing aid or a cochlear implant is necessary for compensation of the sensorineural hearing loss.

Serious sensorineural hearing loss cannot be compensated sufficiently even with the hearing aid. To tackle this problem, a cochlear implant as disclosed in Non-patent Literature 1 has been proposed for remedy for serious sensorineural hearing loss.

The cochlear implant directly applies electric stimuli to an auditory nerve using a multichannel electrode embedded in a cochlea to cause the brain to recognize the sounds. The use of the cochlear implant can recover the auditory sense of a patient whose inner ear is impaired.

CITATION LIST

Non-Patent Literature

[Non-patent Literature 1] Proceedings of the National Academy of Sciences of the United States of America/Nov. 8, 2011/vol. 88/no. 45/18390-18395

SUMMARY OF INVENTION

Technical Problem

However, the cochlear implant cannot cover sounds in the entire range of the audible frequency band of humans. Specifically, the cochlear implant is configured such that a piezoelectric film is induced to vibrate by sound waves coming from the outside to provide electric stimuli to spiral ganglion neurons through multitude microelectrodes provided on the piezoelectric film.

The piezoelectric film is formed in a thin and long trapezoidal shape, and its resonance frequency varies along its length. When sound waves arrive at the piezoelectric film from the outside, a portion of the piezoelectric film that is responsive to the frequencies of the sound waves resonates to cause the microelectrodes provided on the portion to stimulate the spiral ganglion neurons. In short, the piezoelectric film distinguishes the frequencies.

The cochlea is a spiral duct. The cochlear implant is inserted in the cochlea in such a fashion that the longitudinal direction of the piezoelectric film accords with the axial direction of the cochlear duct. The lower the resonance frequencies are, the wider the width of the piezoelectric film is. However, the width of the piezoelectric film cannot be larger than the diameter of the cochlear duct. The piezoelectric film with a width that can allow the cochlear implant to be inserted in a cochlea cannot fully cover sounds in a low frequency band range of the audible frequency band of humans.

Note that another cochlear implant has been also proposed that distinguishes frequencies using a sound processor. This cochlear implant can cover sounds in the entire range of the audible frequency band of humans. However, the sound processor cannot be embedded in the body and is needed to wear. This may limit user's activity in many aspects, thereby imposing a significant burden on the user.

The present invention has been made in view the foregoing and has its object of providing a fully embeddable auxiliary device for sensorineural hearing loss that can cover sounds in the entire range of the audible frequency band of humans.

Solution to Problem

In order to achieve the above object, the present invention provides an artificial sensory epithelium to be embedded in a cochlea of a patient. The artificial sensory epithelium includes a piezoelectric film and multitude microelectrodes arranged on the piezoelectric film. The piezoelectric film is arranged along a basilar membrane in the cochlea. A portion of the piezoelectric film that corresponds to a portion of the basilar membrane that is induced to vibrate by sound waves coming from outside of the cochlea vibrates. A microelectrode of the multitude microelectrodes that is arranged on the portion of the piezoelectric film provides electric stimuli to spiral ganglion neurons.

The artificial sensory epithelium according to the present invention is configured such that the portion of the piezoelectric film that corresponds to the portion of the basilar membrane that is induced to vibrate by the sound waves coming from outside of the cochlea vibrates. This can allow the basilar membrane to distinguish frequencies. Therefore, the artificial sensory epithelium can cover sounds in the entire range of the audible frequency band of humans. Further, the artificial sensory epithelium according to the present invention can be fully embedded in vivo with no external device necessitated for distinguishing frequencies.

It is preferable to provide a support member configured to support the piezoelectric film and be fixable in the cochlea because fitting to the cochlea can be facilitated, and handling can be improved.

Further, it is preferable that the microelectrodes each include a protrusion protruding toward the spiral ganglion neurons. This is favorable because electric stimuli can be readily transmitted to the spiral ganglion neurons.

In this case, when the protrusion has a linear shape, the electric stimuli can be especially readily transmitted to the spiral ganglion neurons.

Note that when the protrusion is formed in a single piece with a corresponding microelectrode, the number of parts can be reduced to favorably reduce the manufacturing cost.

Further, when the piezoelectric film is connected to the basilar membrane, vibration from the basilar membrane is accurately transmitted to the piezoelectric film, which is favorable.

In addition, the piezoelectric film has a thin and long band shape. The piezoelectric film has one end part on which a high-pitch resonance segment is provided, the high-pitch resonance segment resonating with sound waves in a high frequency band range of an audible frequency band of humans. A part of the high-pitch resonance segment on a side of the piezoelectric film has a width larger than a part thereof on an opposite side of the piezoelectric film. With such a configuration, sound waves in a high frequency band range of the audible frequency band of humans can be accurately transmitted to the spiral ganglion neurons, thereby enhancing the audibility.

Advantageous Effects of Invention

The present invention can provide the fully embeddable artificial sensory epithelium that can cover sounds in the entire range of the audible frequency band of humans.

DESCRIPTION OF EMBODIMENTS

Figure 1:
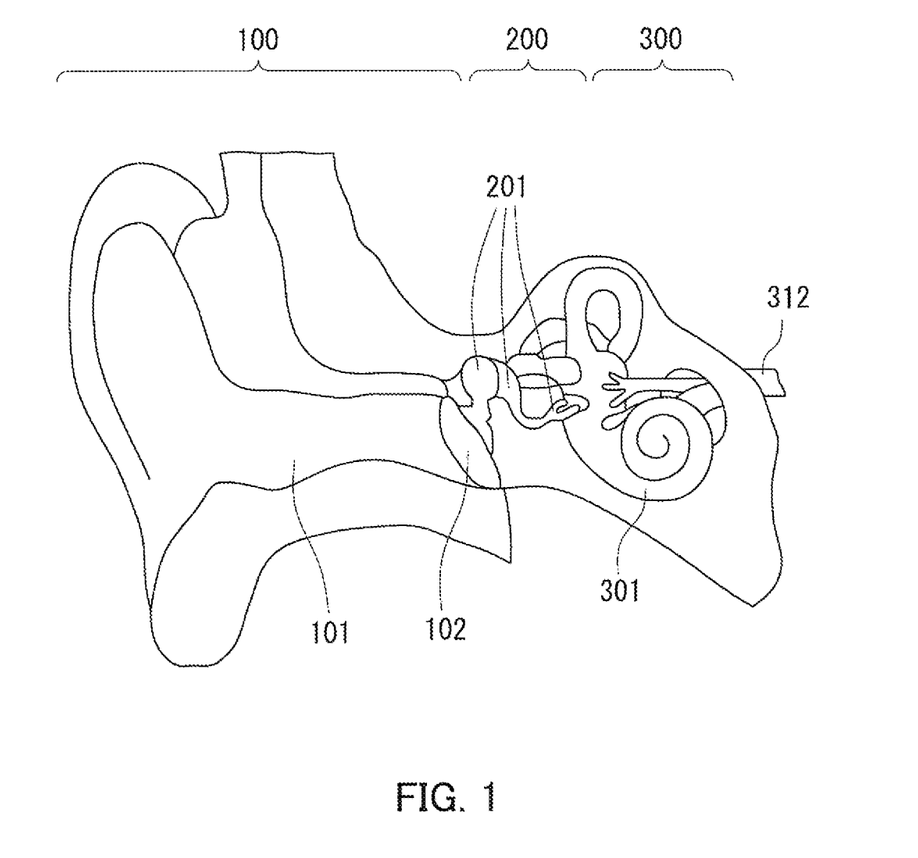
FIG. 1 is a cross sectional view schematically illustrating a structure of an ear.
Figure 2:
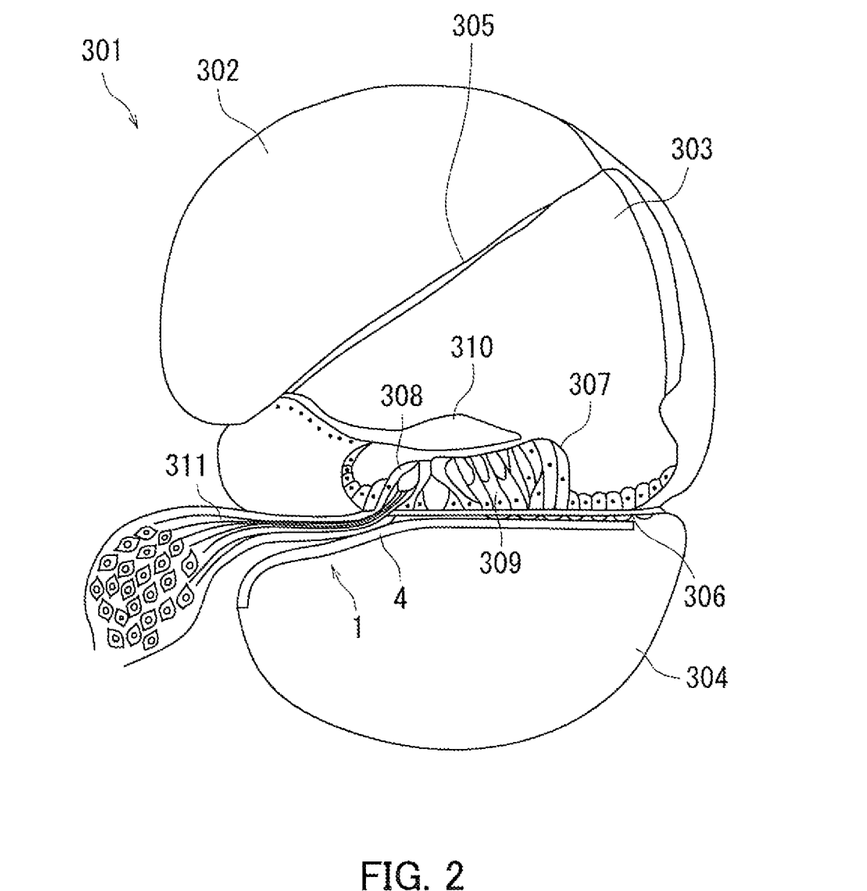
FIG. 2 is a cross sectional view illustrating a structure of a cochlea.

Embodiments of an artificial sensory epithelium according to the present invention will be described below with reference to accompanying drawings. Prior to description of the present embodiment, a basic structure of an ear will be described with reference to FIGS. 1 and 2. FIG. 1 is a cross sectional view schematically illustrating the structure of an ear. FIG. 2 is a cross sectional view illustrating the structure of a cochlea.

An ear as a sense organ administering the auditory sense is divided roughly into an outer ear 100, a middle ear 200, and an inner ear 300, as illustrated in FIG. 1. Sound waves generated outside the ear are guided through an external auditory canal 101 to vibrate a tympanic membrane 102 at the deep end of the external auditory canal 101. An ossicle 201 including three bones transmits the vibration of the tympanic membrane 102 to the inside of the cochlea 301.

The cochlea 301 has a duct shape of about two and a half turn spiral. As illustrated in FIG. 2, the inside of the cochlea 301 is divided into three regions of a scala vestibuli 302, a scala media 303, and a scala tympani 304, each of which is filled with lymph. The scala vestibuli 302 and the scala media 303 are partitioned by a Reissner's membrane 305, while the scala media 303 and the scala tympani 304 are partitioned by a basilar membrane 306.

The basilar membrane 306 is induced to vibrate by sound waves propagating through the outer ear 100 and the middle ear 200. The basilar membrane 306 has portions that are readily vibrate in response to characteristic frequencies of sounds. Large vibrations are induced at the portions responsive to the frequencies of sound waves propagating in the basilar membrane 306.

An organ called Corti's organ 307 is present in the scala media 303. In the Corti's organ 307, two types of cells, inner hair cells 308 and outer hair cells 309 are present and covered with a tectorial membrane 310.

Vibration of the basilar membrane 306 causes vibration of the inner hair cells 308 on the basilar membrane 306. The inner hair cells 308 each include a stereocilia on top thereof and deform through motion relative to the tectorial membrane 310 to cause potential variation.

By contrast, the outer hair cells 309 perform contraction motion to amplify feeble sound stimuli and reduce excessively large sound stimuli, thereby increasing the audibility.

When respective parts of the cochlea 301 receive stimuli, the auditory nerve (a bundle of spiral ganglion neurons 311) 312 (see FIG. 1) transmits the electric signals generated in the cochlea 301 to the brain. The electric signals are sensed on a characteristic frequency basis and finally arrive at the cerebral cortex to be recognized as complex sounds including various frequency components.

Figure 3:
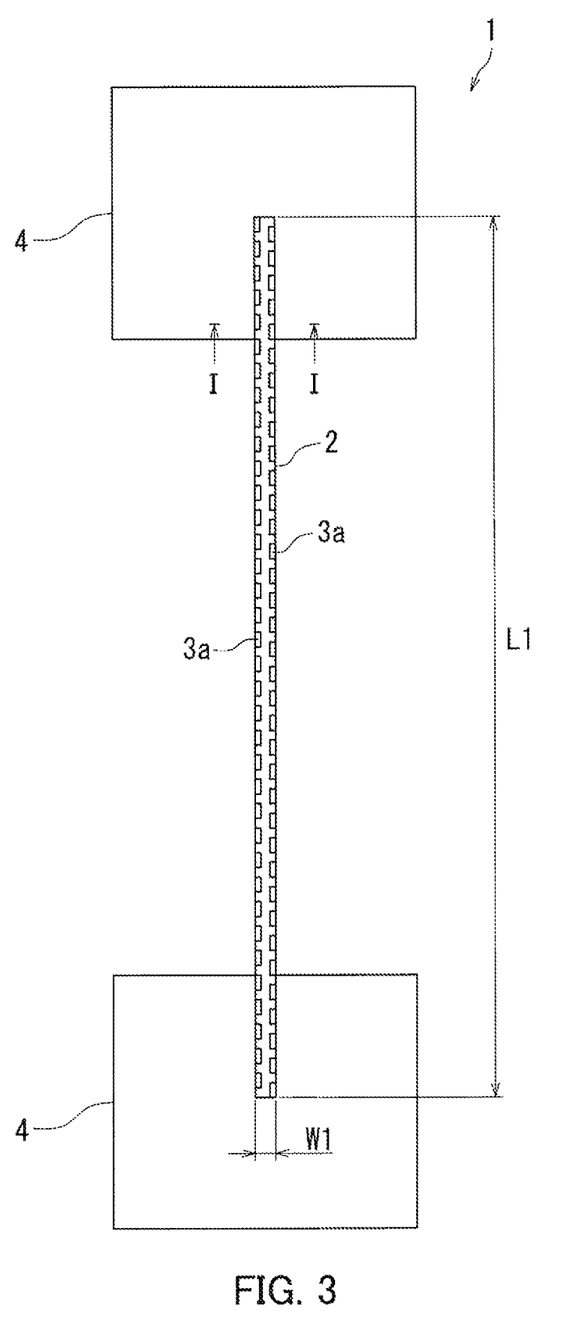
FIG. 3 is a plan view of the first embodiment of the present invention.
Figure 4:
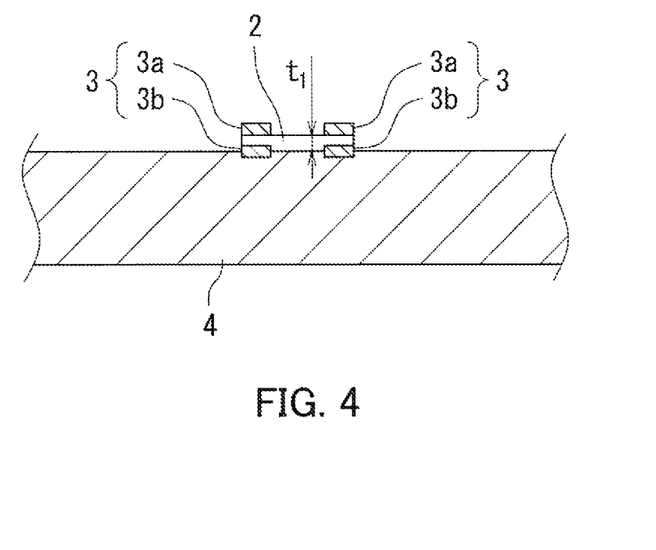
FIG. 4 is a cross sectional view taken along the line I-I in FIG. 3.

The artificial sensory epithelium 1 according to the present embodiment is inserted in the scala tympani 304 of the cochlea 301 with a small space apart from the basilar membrane 306. FIG. 3 is a plan view of the artificial sensory epithelium 1, and FIG. 4 is a cross sectional view taken along the line I-I in FIG. 3. The configuration of the artificial sensory epithelium 1 will be described below with reference to FIGS. 3 and 4.

The artificial sensory epithelium 1 includes a thin and long band-shaped piezoelectric film 2, multitude microelectrodes 3, 3, . . . arranged on the piezoelectric film 2, and support members 4 and 4 that support the opposite end parts of the piezoelectric film 2. The multitude microelectrodes 3, 3, . . . each include a cathode 3a and an anode 3b. The opposite end parts of the piezoelectric film 2 are laid on the tops of the support members 4 and 4. The lower parts of the anodes 3b, 3b, . . . provided below the opposite side edge parts of the piezoelectric film 2 are embedded in the support members 4. Note that the dimension ratio of the piezoelectric film 2 to the support members 4 and that of the microelectrodes 3 to the support members 4 are increased from the respective actual dimension ratios for the sake of better illustration.

The piezoelectric film 2 in the present embodiment is formed of a piezoelectric P(VDF-TrFE) film. When vibration is applied to the piezoelectric film 2, a minute voltage corresponding to strain by the vibration is generated in the piezoelectric film 2. Further, the piezoelectric film 2 is induced to vibrate by sound waves coming from the outside of the cochlea 301. The piezoelectric film 1 is formed such that a portion of the piezoelectric film 2 vibrates that corresponds to a vibrating portion of the basilar membrane 306.

Note that each dimension of respective parts of the piezoelectric film 2 is set such that the piezoelectric film 2 resonates with frequencies higher than those in the audible frequency band of a patient. In the present embodiment, the piezoelectric film 2 has a length L1 of 35 mm, a width W1 of 40 μm or less, and a thickness $t_1$ of 0.4 μm (see FIG. 4) and vibrates in conjunction with the basilar membrane 306 free of influence from sound waves in the audible frequency band of humans.

The microelectrodes 3, 3, . . . are arranged in a staggered manner along the opposite side edge parts of the piezoelectric film 2. The electric stimuli by minute voltage generated in the piezoelectric film 2 are transmitted to the spiral ganglion neurons 311 through the microelectrodes 3.

The microelectrodes 3 in the present embodiment are manufactured by MEMS technique. The dimensions of each electrode (widths along the piezoelectric film 2 in its longitudinal and short directions) are so set that the total charge amount generated in each microelectrode 3 is maximum.

The support members 4 are formed of a material having appropriate flexibility such as silicon, for example. More specifically, the support members 4 can be formed from an SOI wafer. As illustrated in FIG. 2, each support member 4 elastically deforms along the inner surface of the scala tympani 304. The artificial sensory epithelium 1 is fixed and supported in the scala tympani 304 to face the basilar membrane 306. Provision of the support members 4 can facilitate fitting of the artificial sensory epithelium 1 to the cochlea 301 and handling of the artificial sensory epithelium 1.

With reference to FIG. 2, the operation of the artificial sensory epithelium 1 according to the present embodiment will be described next.

The artificial sensory epithelium 1 is fitted in the vicinity of the basilar membrane 306 in a manner that one of the support members 4 is inserted to the scala tympani 304 to make the longitudinal direction of the piezoelectric film 2 accords with the longitudinal direction of the scala tympani 304 of the cochlea 301.

When sound waves in the audible frequency band range of a patient arrives at the basilar membrane 306 from the outside, a portion of the basilar membrane 306 vibrates that is responsive to the frequencies of the sound waves. The vibration propagates to the piezoelectric film 2 of the artificial sensory epithelium 1 to vibrate a portion of the piezoelectric film 2 that corresponds to the vibrating portion of the basilar membrane 306. Thus, the basilar membrane 306 distinguishes the frequencies.

Figure 5A:
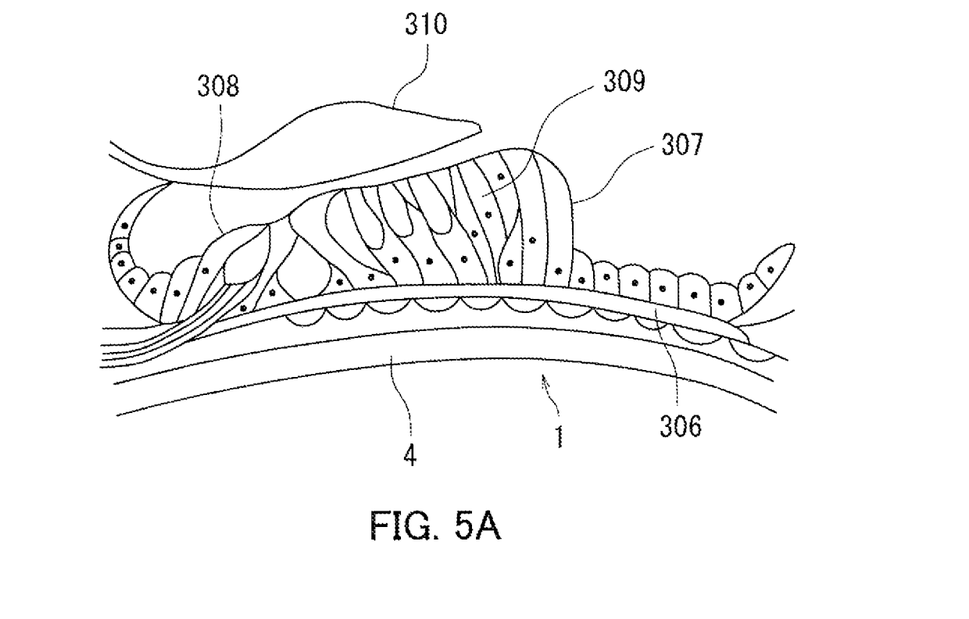
FIG. 5 is an explanatory drawing illustrating the operation in the first embodiment.
Figure 5B:
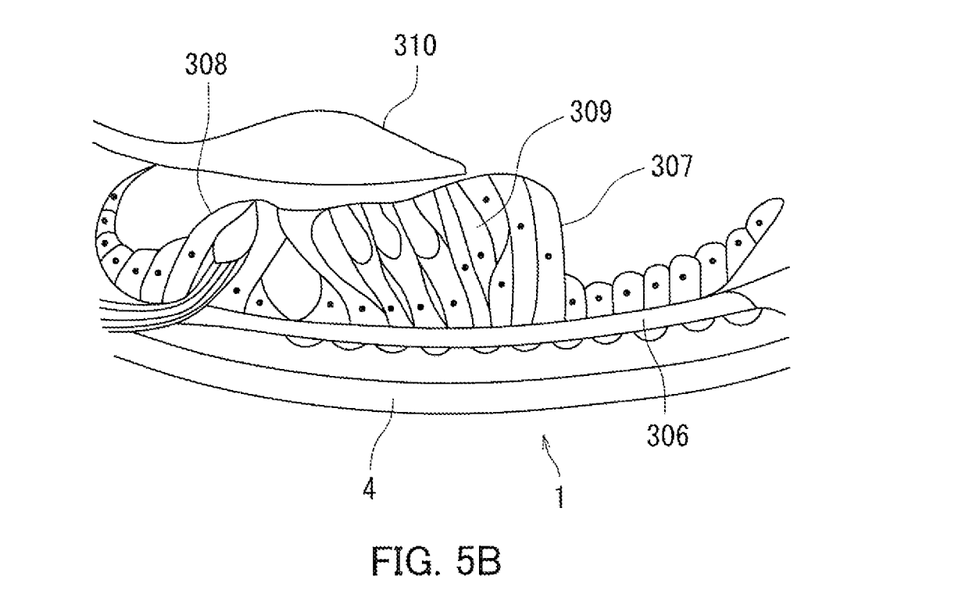

FIG. 5A illustrates the state in which the artificial sensory epithelium 1 is displaced in a given direction, and FIG. 5B illustrates the state in which the artificial sensory epithelium 1 is displaced in the opposite direction to the given direction. Repetition of the displacements is the vibration. The vibration is converted to a voltage by the piezoelectric film 2. Electric stimuli by the voltage are transmitted to the spiral ganglion neurons 311 (see FIG. 2) through the microelectrodes 3 arranged at the vibrating portion of the piezoelectric film 2.

Since the basilar membrane 306 distinguishes frequencies, the artificial sensory epithelium 1 can cover any sounds over the entire range of the audible frequency band of a patient. Further, the artificial sensory epithelium 1 needs no external device for distinguishing frequencies and therefore can be fully embedded in vivo.

Figure 6:
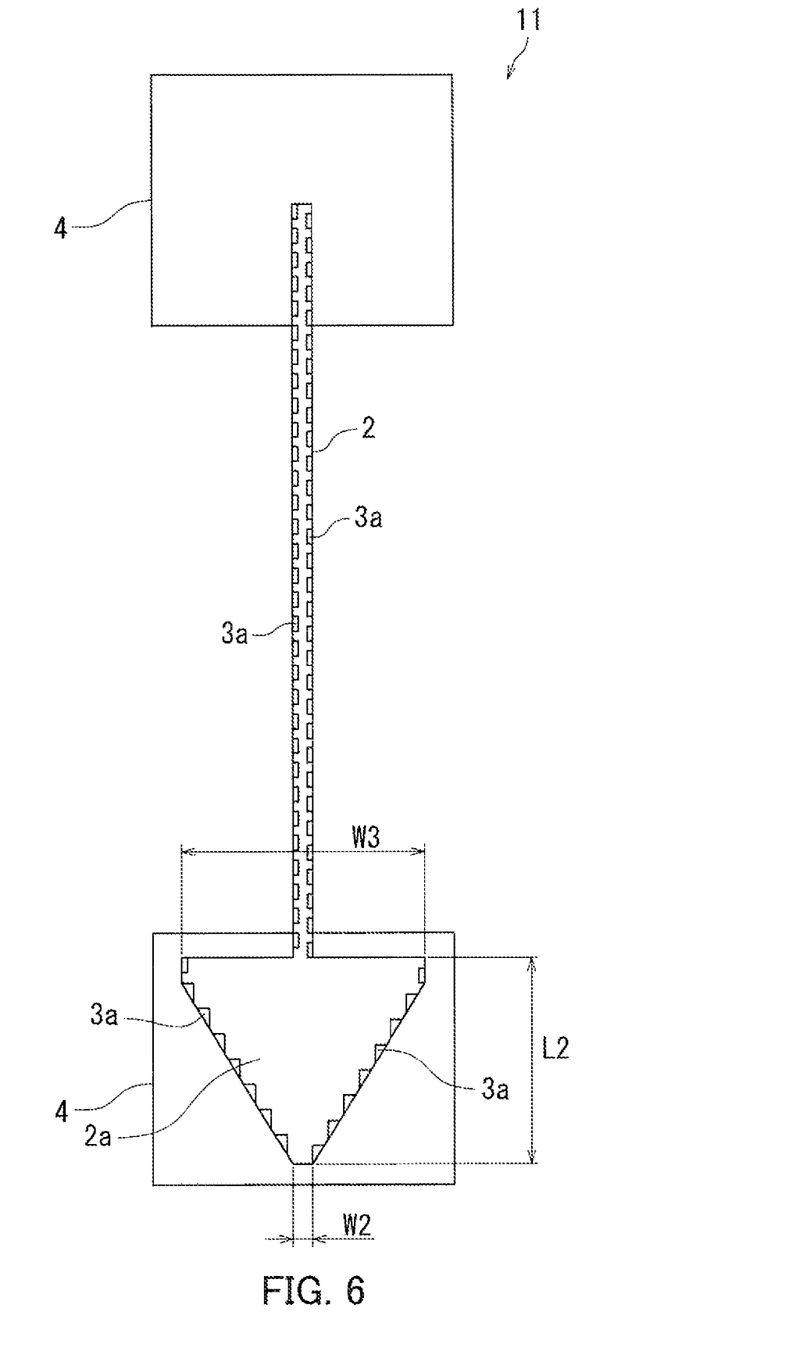
FIG. 6 is a plan view illustrating the second embodiment of the present invention.

The second embodiment of the present invention will be described next. FIG. 6 is a plan view of the second embodiment of the present invention. In the following second and third embodiments, the same reference numerals are assigned to elements corresponding to those in the first embodiment, and duplicate description is omitted. Further, the dimension ratio of the piezoelectric film 2 to the support members 4 and that of the microelectrodes 3 to the support members 4 are increased from the respective actual dimension ratios in FIG. 6 for the sake of better illustration.

A high-pitch resonance segment 2a is provided at one end part of the piezoelectric film 2 in an artificial sensory epithelium 11 in the present embodiment. The high-pitch resonance segment 2a resonates with sound waves in a high frequency band range of the audible frequency band of a patient. A part of the high-pitch resonance segment 2a on the side of the piezoelectric film 2 has a width larger than a part thereof on the opposite side of the piezoelectric film 2. The high-pitch resonance segment 2a is arranged on the inlet side of the cochlea and has a trapezoidal shape that reduces its width as it goes toward the inlet of the cochlea. The high-pitch resonance segment 2a is made of the same material as the piezoelectric film 2. Multitude microelectrodes 3, 3, . . . (only cathodes 3a are illustrated) are provided along the opposite side edge parts of the high-pitch resonance segment 2a in a similar manner to those along the opposite side edge parts of the piezoelectric film 2. The high-pitch resonance segment 2a can be set to have a width W2 of 2 mm at its apex, a width 3W of 4 mm at its base end, and a length L2 of 30 mm. In this case, the high-pitch resonance segment 2a resonates with sound waves in a frequency band range of 5-20 kHz.

The high-pitch resonance segment 2a in the present embodiment directly resonates with sound waves in a frequency band range of 5-20 kHz to generate a voltage.

In a case of sound waves in a high frequency band range, a voltage may be generated more accurately through direct vibration of the piezoelectric film 2 by the sound waves than through vibration propagating from the basilar membrane 306 to the piezoelectric film 2.

In view of the foregoing, in the present embodiment, the high-pitch resonance segment 2a that has a width slim enough to be inserted in the cochlea 301 and resonates with sound waves in a frequency band range of 5-20 kHz is provided at one end part of the piezoelectric film 2, thereby generating a voltage by direct resonance with sound waves in a frequency band range of 5-20 kHz. This can achieve accurate transmission of sound waves in a frequency band of 5-20 kHz to the spiral ganglion neurons, thereby increasing the audibility.

The high-pitch resonance segment 2a of the artificial sensory epithelium 11 resonates with sound waves in a high frequency band range of the audible frequency band of a patient. The width of the high-pitch resonance segment 2a on the side of the piezoelectric film 2 is larger than that on the opposite side of the piezoelectric film 2. The function of the inner hair cells that covers a high-pitch range declines with age. Therefore, the shape of the artificial sensory epithelium 11 is reasonable in medical application.

Figure 7:
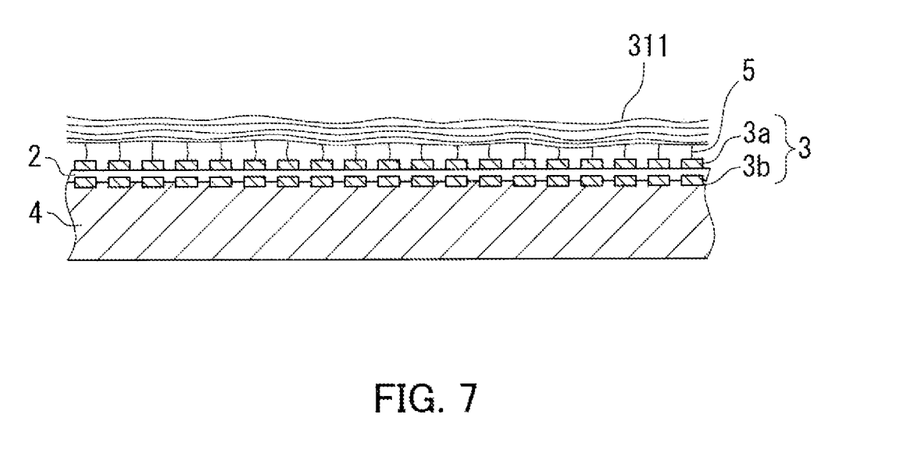
FIG. 7 is a cross sectional view illustrating the main part of the third embodiment of the present invention.

The third embodiment of the present embodiment will be described next. FIG. 7 is a cross sectional view of the main part of the third embodiment of the present invention. Note that FIG. 7 illustrates a cross section of a plane parallel to the longitudinal direction of the basilar membrane 306. The basilar membrane 306 is inherently in a spiral form but illustrated in a linear form in the drawing.

Microelectrodes 3 in the present embodiment each include a protrusion 5 protruding toward the spiral ganglion neurons 311. With this configuration, discharge by a voltage generated in the piezoelectric film 2 is caused at the tip ends of the protrusions 5, thereby enabling achievement of accurate transmission of electric stimuli to the spiral ganglion neurons 311.

The protrusions 5 in the present embodiment are each formed of a short linear member protruding from the corresponding cathode 3a. The protrusions 5 may be made of platinum, for example. Each protrusion 5 can have a diameter of about 3-10 µm and a length of about 3-10 µm, for example.

Note that the shape of the protrusions 5 is not limited to be linear and may be any other shape, for example, a conical shape. Furthermore, a protrusion 5 may be formed in a single piece with a microelectrode 3. In addition, the tip ends of the protrusions 5 may be in contact with or spaced apart from the spiral ganglion neurons 311.

Specific embodiments of the present invention have been described so far. The present invention is not limited to the above embodiments, and various alterations can be made in the above embodiments.

For example, the artificial sensory epithelium is spaced apart from the basilar membrane in the above embodiments, but may be in contact with the basilar membrane.

Further, the artificial sensory epithelium may be connected to the basilar membrane to increase followability of the piezoelectric film to the basilar membrane.

Besides, various alterations of the above embodiments are possible within the scope not departing from the gist of the present invention.

REFERENCE SIGNS LIST 1, 11 artificial sensory epithelium
2 piezoelectric film
2a high-pitch resonance segment
3 microelectrode
4 support member
5 protrusion
301 cochlea
306 basilar membrane
311 spiral ganglion neurons

The invention claimed is:

1. An artificial sensory epithelium to be embedded in a cochlea of a patient, comprising:
a piezoelectric film having a thin and long strip shape; and multitude microelectrodes arranged on the piezoelectric film,
wherein the piezoelectric film is configured to be arranged along a basilar membrane of the cochlea such that a longitudinal direction of the piezoelectric film accords with a longitudinal direction of a scala tympani of the cochlea and vibration of a portion of the basilar membrane propagates to the piezoelectric film when sound wave coming from outside of the cochlea vibrates the portion of the basilar membrane, the portion of the basilar membrane corresponding to a frequency of the sound wave,
the piezoelectric film is configured to vibrate a portion of the piezoelectric film in association with the vibration of the portion of the basilar membrane, the portion of the piezoelectric film corresponding to the portion of the basilar membrane,
the piezoelectric film is configured to induce minute voltage corresponding to strain caused by vibration of the portion of the piezoelectric film, and
the multitude microelectrodes are each configured to provide electric stimuli by the minute voltage to spiral ganglion neurons
wherein the piezoelectric film vibrates in association with vibration of the basilar membrane without receiving influence of sound wave in an audible frequency band of the patient.

2. The artificial sensory epithelium of claim 1, further comprising:

a support member configured to support the piezoelectric film and be fixable in the cochlea.

3. The artificial sensory epithelium of claim 2, wherein the support member includes two support members, one of which supports one of ends of the piezoelectric film and the other of which supports the other of the ends of the piezoelectric film.

4. The artificial sensory epithelium of claim 3, wherein the artificial sensory epithelium is fitted in a vicinity of the basilar membrane in a manner that one of the support members included in the support member is inserted in the scala tympani such that the longitudinal direction of the piezoelectric film accords with the longitudinal direction of the scala tympani.

5. The artificial sensory epithelium of claim 2, wherein the support member is formed from a SOI wafer.

6. The artificial sensory epithelium of claim 2, wherein the support member elastically deforms along an inner surface of the scala tympani of the cochlea, and
the artificial sensory epithelium is fixed and supported to the scala tympani at a location opposite to the basilar membrane.

7. The artificial sensory epithelium of claim 1, wherein the microelectrodes each include a protrusion protruding toward the spiral ganglion neurons.

8. The artificial sensory epithelium of claim 7, wherein the protrusion is a linear member.

9. The artificial sensory epithelium of claim 7, wherein the protrusion is formed in a single piece with a corresponding microelectrode.

10. The artificial sensory epithelium of claim 7, wherein the protrusion performs discharge between a tip end of the protrusion and the spiral ganglion neurons by the minute voltage generated in the piezoelectric film.

11. The artificial sensory epithelium of claim 7, wherein the protrusion is made of platinum.

12. The artificial sensory epithelium of claim 1, wherein the piezoelectric film has one end part on which a high-pitch resonance segment is provided, the high-pitch resonance segment resonating with sound waves in a high frequency band range of an audible frequency band of the patient, and
a part of the high-pitch resonance segment on a side of the piezoelectric film has a width larger than a part thereof on an opposite side of the piezoelectric film.

13. The artificial sensory epithelium of claim 1, wherein the piezoelectric film has a dimension such that the piezoelectric film resonates at a frequency higher than an audible frequency band of the patient.

14. The artificial sensory epithelium of claim 1, wherein the microelectrodes are arranged in a staggered manner along opposite side edge parts of the piezoelectric film.

* * * * *